United States Patent [19]
Matsumura et al.

[11] 4,102,563
[45] Jul. 25, 1978

[54] EYE FUNDUS CAMERA FREE FROM UNDESIRED REFLECTED AND DIFFUSED LIGHT BEAMS

[75] Inventors: Isao Matsumura, Yokohama; Takeshi Kuwayama, Atsugi; Yoshimi Kohayakawa, Yokohama, all of Japan

[73] Assignee: Canon Kabushiki Kaisha, Tokyo, Japan

[21] Appl. No.: 744,809

[22] Filed: Nov. 24, 1976

[30] Foreign Application Priority Data

Dec. 1, 1975 [JP] Japan ................................. 50-143729

[51] Int. Cl.² ............................................. A61B 3/10
[52] U.S. Cl. ......................................... 351/7; 351/16; 354/62
[58] Field of Search ........................ 351/7, 13, 14, 16; 354/62

[56] References Cited

U.S. PATENT DOCUMENTS

| | | | |
|---|---|---|---|
| 3,594,071 | 7/1971 | Okajima ................................... | 351/7 |
| 3,851,954 | 12/1974 | Kato et al. ................................ | 351/7 |
| 3,925,793 | 12/1975 | Matsumara et al. .................. | 351/7 X |

Primary Examiner—Paul A. Sacher
Attorney, Agent, or Firm—Toren, McGeady and Stanger

[57] ABSTRACT

The present invention relates to an eye fundus camera free from undesired reflected and diffused light beams. The camera uses a photographic optical system including an objective lens, a reflecting means, an aperture means, a photographic lens system for imaging the eye fundus to be inspected in sequence on a photographic plane and an illumination optical system including at least a light source, a relay lens and a ring-shaped aperture. The optical system leads the light beam from the light source to the eye to be inspected through the reflecting means and the objective lens, whereby the ring-shaped aperture is positioned in the illumination optical system in such a manner that the image of the ring-shaped aperture is formed near the iris in the eye to be inspected while the aperture is positioned in such a manner that the conjugate position of the aperture with reference to the objective lens is near the cornea to the eye to be inspected. The undesired reflected and diffused light beam out of the illumination light beam taking place in the eye to be inspected is thereby eliminated.

6 Claims, 9 Drawing Figures

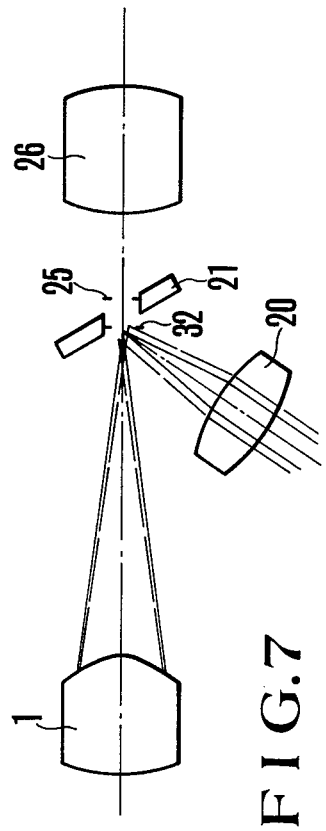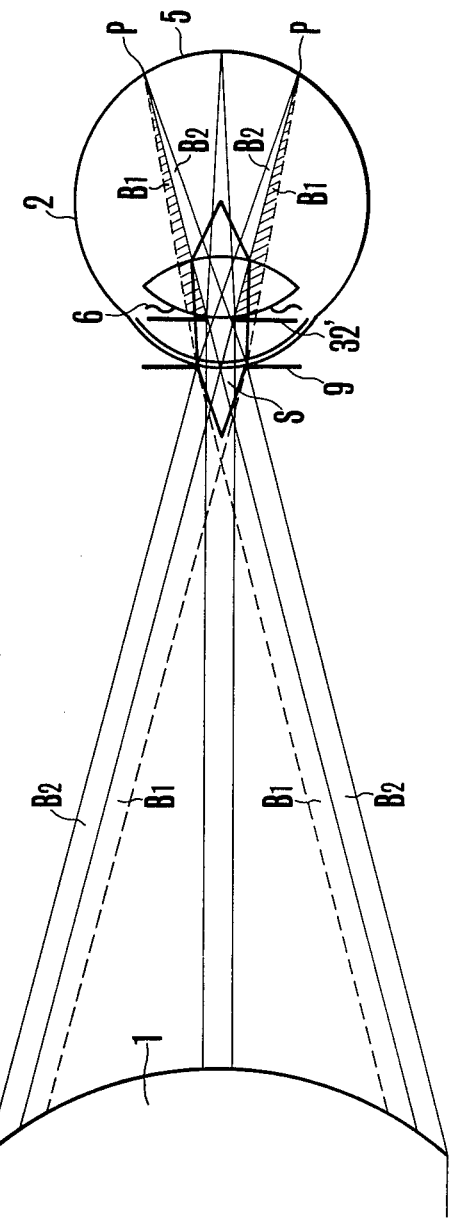

EYE FUNDUS CAMERA FREE FROM UNDESIRED REFLECTED AND DIFFUSED LIGHT BEAMS

BACKGROUND OF THE INVENTION

The present invention relates to an eye fundus camera capable of effectively eliminating undesirable reflected and diffused light beams produced by the lens of the eye to be inspected, and eliminating undesired reflected and diffused light beams resulting from the interaction of the illumination light beam and the cornea of the eye to be inspected.

It is well known that when an eye to be inspected is illuminated with an illumination light beam at the time of taking a picture of the eye fundus, a part of the illumination light beam is reflected on the surface of the cornea and the lens or diffused in them. There is a possibility that the reflected and the diffused light beams become mixed with the light beam reflected on the eye fundus for photographic or the observational purpose so as to produce flair light or ghost images. It is therefore desirable that the aforementioned reflected or diffused light beams should be removed. Until now the undesired light beams reflected primarily from the surface of the cornea has effectively been removed by means of a ring illumination method. However, little interest is paid to the removal of the light beams reflected on the lens and the cornea and to the light beams diffused in the lens, which light beams are weak as compared with the light beam reflected on the surface of the cornea. However, along with the recent demand for a wide angle eye fundus camera and a clearer photograph of the eye fundus, the light beams diffused in the cornea, the light beams reflected on the lens and the light beams diffused in the lens can no longer be disregarded.

One of the means for removing the undesired light beam reflected on and diffused in the lens is disclosed by the U.S. Pat. No. 3,851,954. In accordance with this method, a black spot is provided in the illumination light beam in such a manner that the undesired reflected light beam is removed by means of the black spot and the ring-shaped aperture.

SUMMARY OF THE INVENTION

An object of the present invention is to offer an eye fundus camera capable of removing the undesired reflected and the undesired diffused light beams by means of a novel means different from the above mentioned conventional black spot.

Another object of the present invention is to offer an eye fundus camera capable of effectively leading the light beam incident on the eye to be inspected from the illumination optical system to the eye fundus of the eye to be inspected.

The present invention intends to achieve the above mentioned purpose by effectively utilizing a conventional ring-shaped aperture. According to the prior art, an image of this aperture is formed near the cornea of the eye to be inspected, and an aperture for removing the undesired light beam reflected from the eye to be inspected cooperates with the ring-shaped aperture. For this purpose, the optical system of the eye fundus camera in accordance with the present invention is so designed that the image of the ring-shaped aperture formed on the front surface of the eye to be inspected can effectively be separated from the image of the aforementioned aperture by means of the objective lens.

More particularly, in the eye fundus camera in accordance with the present invention the image of the ring-shaped aperture is formed near the iris while the image (namely at the conjugate position of the aperture with reference to the objective lens) of the aperture is formed in such a manner that the illumination light beam is effectively led to the eye fundus.

In accordance with the present invention the undesired reflected light beam is all the more effectively removed by combining the means of the present invention with the above mentioned black spot.

Further in accordance with the present invention the formation of the flare light and of the ghost images with the illumination light beam on and in the camera and the lens is completely avoided by combining a proper means with the device including the combination of the means of the present invention and the above mentioned black spot means.

BRIEF DESCRIPTION OF DRAWINGS:

FIG. 6 shows another embodiment of the eye fundus camera in accordance with the present invention near a mirror with an opening in partial enlargement.

FIG. 7 shows the eye fundus camera shown in FIG. 6 near the eye to be inspected in partial enlargement.

Figure 1:
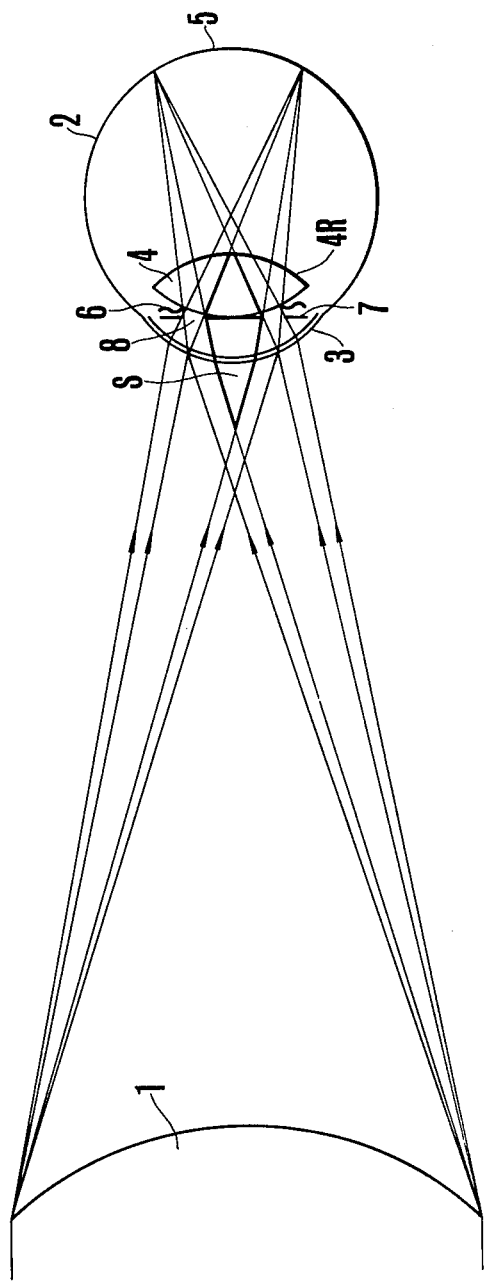
FIGS. 1 and 2 respectively show an eye fundus camera, in accordance with the present invention, in the neighborhood of the eye to be inspected and in partial engagement therewith for explaining the principle of the present invention.
Figure 2:
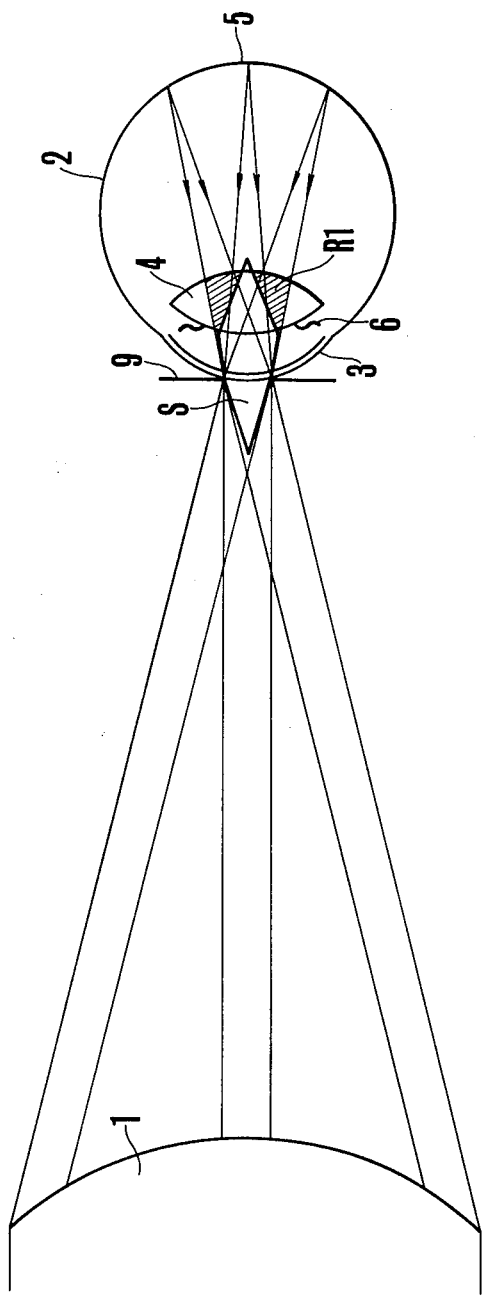

DESCRIPTION OF THE PREFERRED EMBODIMENTS:

FIGS. 1 and 2 respectively show the objective lens 1 and the eye 2 to be inspected in enlargement for explaining the principle of the present invention, whereby FIG. 1 shows the optical path of the light beam incident on the eye to be inspected, while FIG. 2 shows the optical path of the light beam coming out from the eye fundus. As is clear from FIG. 1 the image 7 of the ring-shaped aperture formed by means of the illumination optical system is formed near the iris 6. This means that the place which the illumination light beam can not reach (hereinafter called shaded portion S) can be moved up to the rear surface 4R of the lens 4 by bringing the position of the image 7 of the ring-shaped aperture close to the lens 4. In consequence, the area of the shaded portion S in which undesired reflected light beams or undesired diffused light beams are located is increased. Thus, it is desired that as mentioned above the image 7 of the ring-shaped aperture should be formed near the iris 6. The reason is that when the image 7 of the ring-shaped aperture is displaced further toward the eye fundus 5 the shaded portion S covering the camera becomes smaller so that the influence of the reflection on the surface of the cornea 3 becomes larger, while when the image 7 of the ring-shaped aperture is displaced further toward the cornea the shaded portion S covering the lens 4 becomes smaller, so that the influence of the undesired light beam reflected or diffused on the lens 4 becomes larger. Further, the light beam can illuminate the eye fundus efficiently by forming the image 7 of the ring-shaped aperture near the iris 6. Namely the light beam is narrowest at the opening 8 of the image of the ring-shaped aperture in such a manner that the intensity of the light beam per unit area is largest. On the other hand, if the image of the ring-shaped aperture is formed near the iris 6 restricting the illumination light beam reaching the eye fundus, the light beam which passes through the opening 8 of the ring-shaped aperture but is interrupted by the iris 6 becomes reduced in intensity. Thus the illumination light beam can be led to the eye fundus efficiently.

It is desired that, as is shown, an aperture should be provided in such a manner that the image 9 of the aperture formed by the objective lens 1 near the cornea 3 is contained in the aforementioned shaded portion S. If the image 9 of the aperture should be formed near the image 7 of the ring-shaped aperture, the influence of the light beam reflected from the surface of the cornea or diffused in the cornea would become larger. If, on the other hand, if the image 9 of the aperture should be displaced toward the side of the objective lens 1, the opening of the aperture would become smaller in order to remove the light beams reflected from the cornea 3 in such a manner that the intensity of the light beam incident on the photographic lens out of the light beam reflected on the eye fundus would be less.

Further it is effective to take a picture of the eye fundus with a wide angle lens to separate the image 7 of the ring-shaped aperture from that 9 of the aperture efficiently. Namely, if in FIG. 2 the image 9 of the aperture should be displaced toward the lens 4, the light beams coming from positions on the eye fundus that are considerably displaced from the optic axis of the system would have to pass through the portion of the cornea not covered with the aforementioned shaded portion S when the light beam should pass through the cornea 3. This means that the influence of the undesired light beams reflected or diffused by the cornea would become larger, whereby wide angle photography or observation would be impossible. Thus, it is desirable that the image 9 of the aperture by means of the objective lens 1 should be formed near the cornea 3 in order that the wide angle photography or observation of the eye fundus can be achieved while there is little influence of the undesired light beam reflected from or diffused in the cornea.

Figure 3:
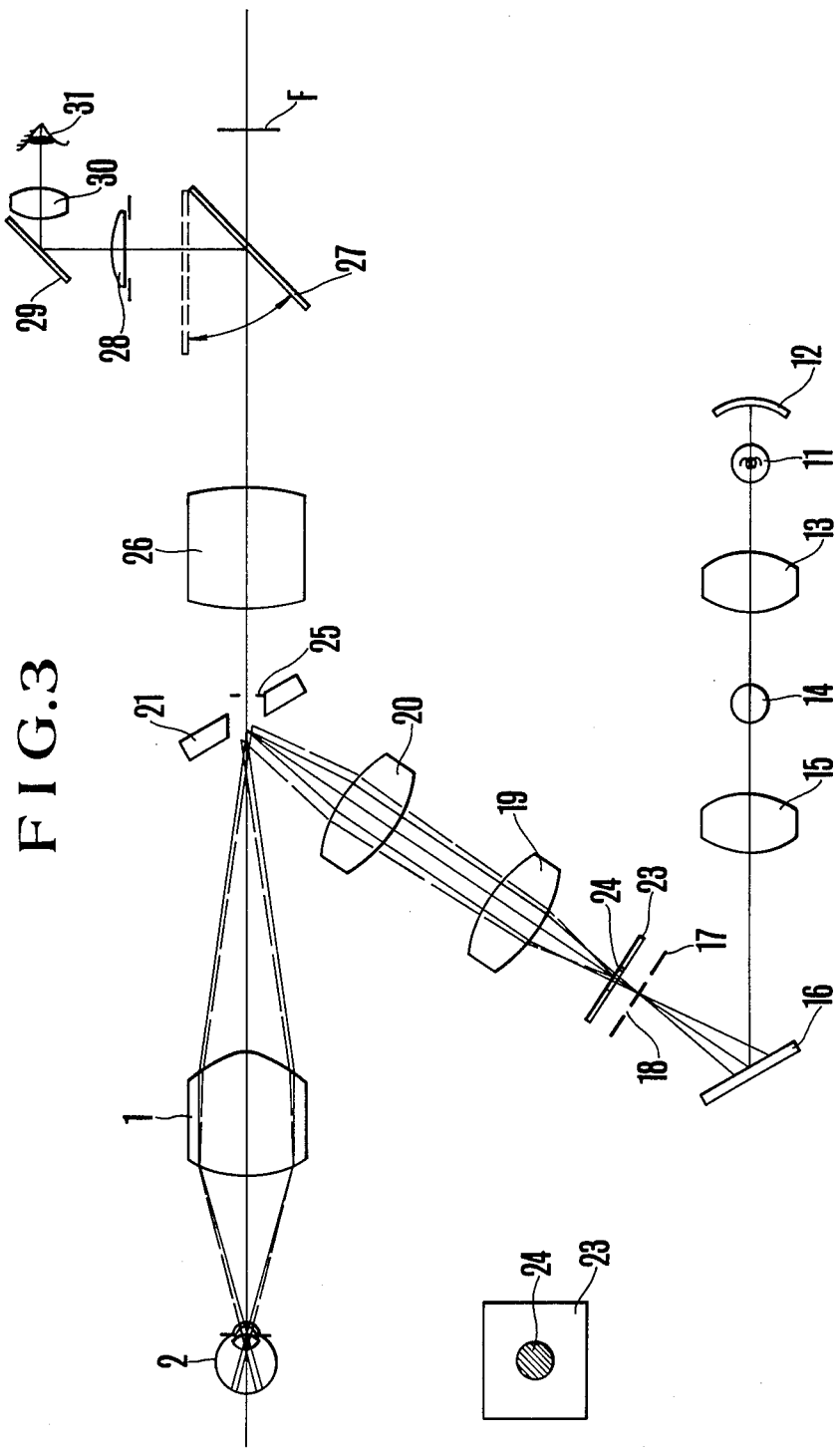
FIG. 3 shows an embodiment of the optical system of the eye fundus camera in accordance with the present invention.
Figure 4:
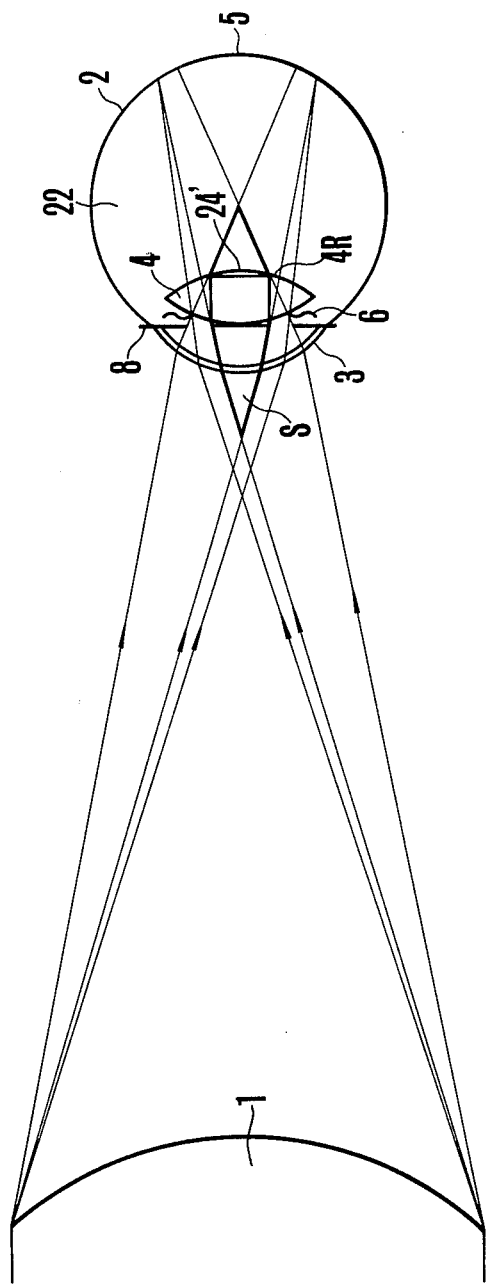
FIGS. 4 and 5 respectively show the optical system of the eye fundus camera shown in FIG. 3 in the neighborhood of the eye to be inspected, and in partial engagement therewith.
Figure 5:
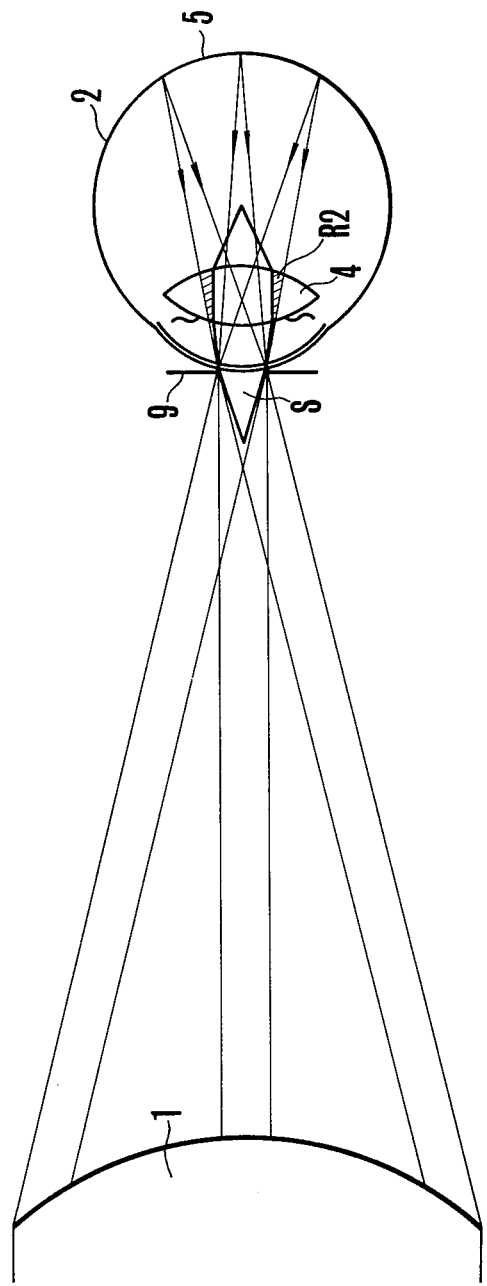

By means of the above mentioned effective arrangement of the ring-shaped aperture and the aperture, the flair light and the ghost images can be decreased, while there is a possibility that in the area R1 in oblique lines in FIG. 2 the influence of light reflected on the surface of the lens or diffused in the lens may be confined. In order to make the area R1 smaller, it is desirable to apply the present invention together with the aforementioned black spot means as is shown in FIGS. 3, 4 and 5. FIG. 3 shows an embodiment of the optical system in which the present invention and the black spot means are applied, while FIGS. 4 and 5 respectively show the objective lens 1 and the eye 2 to be inspected in enlargement.

In FIGS. 3, 4 and 5 the light beam coming from the light source 11 such as a tungsten lamp including that reflected by the mirror 12 is once condensed on the strobe light tube 14 by means of the condenser lens 13 and then on the ring-shaped aperture 17 by means of the condenser lens 15 and the reflecting mirror 16. The ring-shaped aperture 17 possesses a ring-shaped permeable portion 18, whereby the light coming from the permeable portion 18 of the ring-shaped aperture as the secondary light source once forms the image of the ring-shaped aperture 17 near the mirror 21 with an opening. The light beam reflected by means of the mirror 21 with an opening again forms the image 7 of the ring-shaped aperture on the iris 6 of the eye 2 to be inspected by means of the objective lens 1 and then illuminates the eye fundus 5 through the lens 4 and the vitreous body 22. On the other hand the light shading plate 23 with a circular black spot 24 is provided closer to the mirror 21 with a circular black spot 24 than the ring-shaped aperture 17 in the illumination optical system so that the image 24' of the black spot 24 is formed near the rear surface 4R of the lens 4 in the eye 2 to be inspected through the relay lenses (19, 20), the mirror 21 with an opening and the objective lens 1. In this case the shaded portion S is projected further toward the eye fundus than in case there is no image 24' of the black spot.

On the other hand the light beam reflected on the eye fundus 5 passes through the objective lens 1 and then the aperture 25. As mentioned above the aperture 25 is positioned in such a manner that the image 9 of the aperture 25 by means of the objective lens 1 is formed on the cornea 3 of the eye to be inspected. The light beam coming from the aperture 25 is observed by the observer through the photographic lens 26, the spring up mirror 27, the field lens 28, the direction changing mirror 29 and the eye piece lens 30. Further, at the time of taking a picture of the eye fundus, the mirror 27 is lifted up while at the same time the strobe light tube 14 is actuated so as to expose the film F.

As is clear from FIG. 5, even in this case for the light beam reflected from the eye fundus there is a possibility of the influence of the flare light and the ghost images from the lens 4 in the area R2 in oblique lines. It is possible to absolutely remove the undesired light beam reflected or diffused by the lens and the cornea by means of avoiding the influence of the area R2 shown in FIG. 5. In order to achieve the above mentioned purpose, the present invention applies a means for eliminating the light beams reflected on the eye fundus and passing through the area R2 in oblique lines. For this purpose, as is shown in FIG. 6, another aperture 32 is provided near the mirror 21 with an opening. FIG. 6 shows the optical system near the mirror with an opening in partial enlargement, whereby what is different from FIG. 3 is only the aperture 32. FIG. 7 shows how the image 32' of the aperture 32 is formed near the iris 6 by means of the objective lens. Further, FIG. 7 shows how the light beam is reflected from the eye fundus. Hereby the formation of the shaded portion S shown in FIG. 7 is identical with the case shown in FIG. 4 so that the explanation is omitted here. The aperture 32 is provided in such a manner that, as is shown in FIG. 7, out of the light beam reflected at the point P on the eye fundus only the component $B_1$ passing through the area R2 in oblique lines shown in FIG. 5 is interrupted by means of the aperture 32. Hereby the above mentioned point P is the position at the widest angle of the eye fundus to be photographed. Hereby it is desirable that the aperture 32 for interrupting the above mentioned light beam $B_1$ should be positioned in such a manner that the image 32' of the aperture 32 is formed near the lens 4 (preferably near the iris) by means of the objective lens 1. The reason is that in case the image 32' of the aperture 32 should be close to the image 9 of the aperture 25 in the interrupted state of the light beam $B_1$, the aperture 32 would also interrupt the effective light beam $B_2$ free from the undesired light beam, out of the light means coming from the point P. On the other hand, the displacement of the image 32' of the aperture 32 toward the eye fundus necessitates the displacement of the aperture shown in FIG. 6 toward the objective lens 16. In consequence, it is undesirable that the image 32' of the aperture 32 lie too close to the eye fundus, because it would be highly probable that the aperture 32 should interrupt the light beam from the illumination optical system. In consequence, it is desirable that the aperture 32 should be provided in such a manner that the image 32' of the aperture 32 is formed near the lens 4 by means of the objective lens 1. The light beam reflected from the eye fundus, and passing the portion of the lens 4 distant from its center is interrupted by means of the image 32' of the aperture 32. The light beam incident on the photographic lens 1 is little influenced by the coma aberration of the eye to be inspected so that the resolving power can further be increased.

Figure 8:
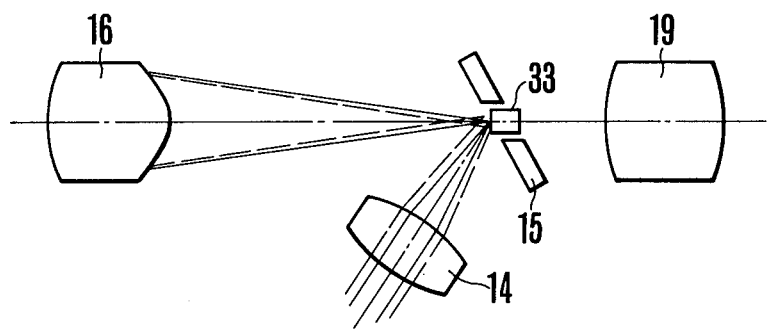
FIGS. 8 and 9 respectively show another embodiment of the optical system shown in FIG. 6.
Figure 9:
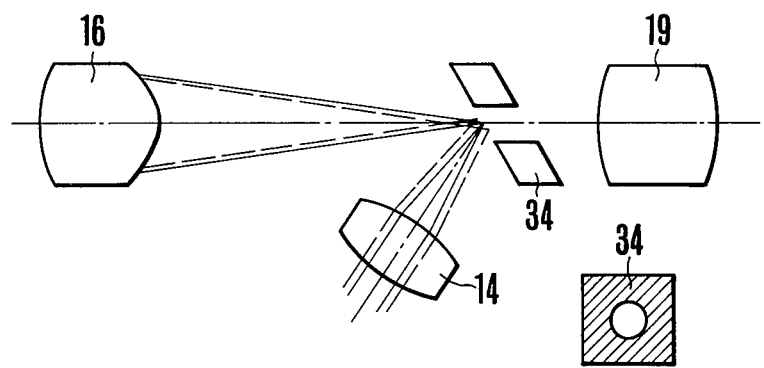

In the embodiment shown in FIG. 6, two apertures (25, 32) are used. It is also possible to replace the apertures (25, 32) by a cylindrical aperture 32 with a length equal to the distance between the above mentioned apertures (25, 32) as is shown in FIG. 8. In order to replace the apertures (25, 32) with the both ends of the opening of the mirror 21, nearly the same effect as that in case of the apertures (25, 32) can be achieved by making the mirror 34 with an opening thicker as is shown in FIG. 9.

What is claimed is:

1. An eye fundus camera free from undesired reflected and diffused light beams comprising:
    a photographing optical system for photographing the fundus of an eye to be inspected and being provided with a photographing aperture;
    an illuminating optical system for illuminating the fundus of the eye to be inspected through a ring-shaped aperture;
    a first optical means in said illuminating optical system for forming an image of the ring-shaped aperture in the iris of the eye to be inspected;
    a second optical means in said photographing optical system for conjugating the photographing aperture with the cornea of the eye to be inspected so as to eliminate diffused and reflected light beams from the cornea of the eye to be inspected.

2. An eye fundus camera in accordance with claim 1, which further comprises a plate in said illuminating optical system having a black spot, a third optical means for forming an image of said plate near a plane on the fundus side of the crystalline lens of the eye to be inspected.

3. An eye fundus camera in accordance with claim 2, wherein said photographing system is provided with a second aperture, and further comprising a fourth optical means for substantially conjugating optically the second aperture with the iris of the eye to be inspected.

4. An eye fundus camera free from undesired reflected and diffused light beams comprising:
    a photographic optical system including an objective lens, a reflecting means with an opening, a first aperture and a photographic lens system, said objective lens, reflecting means, first aperture and photographic lens system being serially arranged with said objective lens closest to the eye to be inspected;
    said first aperture substantially conjugating with a cornea of the eye to be inspected with respect to said objective lens for preventing the light beam diffused by the cornea of the eye to be inspected;
    an illuminating optical system for illuminating the fundus of the eye to be inspected including a light source, a relay lens system and a ring-shaped aperture, the illuminating light beam from the illuminating optical system being directed toward the eye to be inspected through said reflecting means and objective lens;
    said illuminating optical system further comprising means for substantially conjugating said ring-shaped aperture with the iris of the eye to be inspected with respect to the optical system disposed between said ring-shaped aperture and the eye to be inspected and for leading said illuminating light beam effectively to said fundus and for preventing the light beam reflected and diffused by the crystalline lens of the eye to be inspected.

5. An eye fundus camera in accordance with claim 4, wherein a plate with a black spot is provided in said illuminating optical system, said plate with said black spot substantially conjugating with the surface on the fundus side of the crystalline lens of the eye to be inspected with respect to the optical system disposed between said plate and the eye to be inspected for preventing the light beam diffused by said crystalline lens.

6. An eye fundus camera in accordance with claim 5, wherein a second aperture is provided at a position between said first aperture and said objective lens, said second aperture substantially conjugating with the iris of the eye to be inspected with respect to said objective lens.

* * * * *